United States Patent [19]

Laba

[11] Patent Number: 4,659,571

[45] Date of Patent: Apr. 21, 1987

[54] COMPRESSED POWDER FORMULATION CONTAINING ORGANOPHILIC CLAY AND A PROCESS FOR MAKING THE FORMULATION

[75] Inventor: Dennis Laba, Middlesex, N.J.

[73] Assignee: NL Industries, Inc., New York, N.Y.

[21] Appl. No.: 713,897

[22] Filed: Mar. 20, 1985

[51] Int. Cl.$^4$ .......................... A61K 7/32; A61K 7/34; A61K 7/36; A61K 7/38

[52] U.S. Cl. .................. 424/65; 252/522 R; 424/DIG. 5; 424/63; 424/66; 424/67; 424/68; 424/69; 424/73; 514/188; 514/558; 514/642; 514/643; 514/844; 514/947; 514/948; 514/949; 514/951; 514/953; 514/965

[58] Field of Search ................ 424/DIG. 5, 69, 68, 424/66; 514/930, 844, 770, 947, 948, 949, 951, 953, 965

[56] References Cited

U.S. PATENT DOCUMENTS

| | | | |
|---|---|---|---|
| 3,227,657 | 1/1966 | Haden, Jr. | 514/770 |
| 3,856,014 | 12/1974 | Yamauchi | 424/28 |
| 4,116,866 | 9/1978 | Finlayson | 514/770 |
| 4,425,328 | 1/1984 | Nabial | 424/DIG. 5 |
| 4,431,673 | 2/1984 | Goldner et al. | 424/DIG. 5 |
| 4,434,075 | 2/1984 | Mardis et al. | 106/27 |
| 4,434,076 | 2/1984 | Mardis et al. | 106/27 |
| 4,440,741 | 4/1984 | Marschner | 424/DIG. 5 |
| 4,477,431 | 10/1984 | Suffis | 424/69 |
| 4,517,112 | 5/1985 | Mardis et al. | 106/27 |
| 4,526,780 | 7/1985 | Marschner et al. | 514/770 |

FOREIGN PATENT DOCUMENTS

| | | | |
|---|---|---|---|
| 640644 | 8/1962 | Italy | 424/69 |
| 004355 | 1/1980 | Japan | 424/69 |
| 0034609 | 4/1981 | Japan | 424/69 |
| 48201 | 1/1982 | Japan | 424/69 |
| 0109706 | 7/1982 | Japan | 424/69 |
| 2096891 | 10/1982 | United Kingdom | 424/65 |

OTHER PUBLICATIONS

Barr, American Perfumer and Cosmetics, 2/1963, vol. 78, No. 2, pp. 37-45 and 48.

*Primary Examiner*—Dale R. Ore
*Attorney, Agent, or Firm*—Burns, Doane, Swecker & Mathis

[57] ABSTRACT

A compressed powder formulation which consists essentially of an organophilic clay and at least one topical agent. The formulation maintains its physical integrity upon handling thereby permitting the preparation of the formulation in the form of self-supporting sticks and exhibits an acceptable level of payout. Additionally, the formulation retains an acceptable level of payout even when contacted with water. A process of making the formulation by compressing a powderous mixture is also set forth.

28 Claims, No Drawings

COMPRESSED POWDER FORMULATION CONTAINING ORGANOPHILIC CLAY AND A PROCESS FOR MAKING THE FORMULATION

BACKGROUND OF THE INVENTION

1. Field of the Invention

The present invention relates to a compressed powder formulation containing a substantial amount of at least one organophilic clay. The present invention also relates to a process for making the formulation.

2. Description of the Prior Art

Known antiperspirant solid formulations basically fall into four categories, namely suspensoid sticks, wax-based sticks, gelled sticks and pressed powder sticks. However, each of these types of sticks possesses certain disadvantages. A typical suspensoid or suspension stick is described in U.S. Pat. No. 4,126,679 and consists of a powdered antiperspirant active ingredient suspended in a base consisting of a fatty alcohol and a liquid siloxane. To prepare the base, the ingredients are heated to a critical temperature range, cooled at a critical rate and poured at a temperature just above the congealing point of the mass. Once the stick is cast, it will very often have voids in the middle caused by uneven cooling rates within the stick. Further processing is needed to eliminate the voids. As should be apparent from this process description, the currently marketed suspensoid sticks are both energy and time intensive.

A further type of suspensoid stick is disclosed in U.S. Pat. No. 4,440,742. The stick consists essentially of an alkali metal bicarbonate and an optional suspending agent which is dispersed in a soap which comprises a polyhydric alcohol, alone or with a monohydric alcohol, which is gelled with an alkali metal salt of a fatty acid. The suspending agent can be colloidal or pyrogenic silica, colloidal alumina, hydrophobically treated clays or colloidal magnesium aluminum silicates.

As their name indicates, wax-based sticks contain a substantial amount of wax and therefore exhibit several inherent disadvantages. The first is the difficulty of washing the wax residue left on the clothes which can cause discoloration. The second disadvantage has to do with the naturally hydrophobic character of the waxes. That is, since the commonly used active ingredients must go into solution before they exert their effects, the wax-coating of the powered antiperspirant or deodorant ingredients inhibits the perspiration from dissolving such ingredients. This naturally decreases the efficiency of the wax-based sticks.

The gelled sticks, such as based on sodium stearate as set forth in U.S. Pat. No. 4,322,400 or based on dibenzaldehyde-monosorbitol acetal as set forth in U.S. Pat. No. 4,154,816, often suffer from a stability problem when used in combination with an antiperspirant agent. The acidity of common antiperspirant agents exemplified by aluminum chlorohydrate and aluminum zirconium compounds tend to break down the sodium stearate gel structure or the dibenzaldehyde thereby deleteriously affecting the performance of the stick. In an attempt to alleviate the problem, a complexed structure of aluminum chlorohydrate and sodium chlorhydroxy lactate has been traditionally used with a sodium stearate gel, but since the compound has been rendered basic due to the sodium lactate association, it loses a significant portion of its antiperspirant activity.

Attempts have also been made in the past to provide dry, pressed powder sticks useful in the cosmetics and toiletries market. These efforts have been focused in basically two directions, the withdrawal of the processing solvents after preparation and direct-compression. The withdrawal or evaporation of the solvents after stick formation as described in U.S. Pat. No. 4,414,200 is still energy or time consuming because a suspensoid stick must still be formed before the additional process step of evaporation.

Traditional direct-compression sticks, because of the hydrophillic character of the bases used, tend to absorb water from the air or moist environments like a bathroom or human axilla. This water both swells, the base, causing it to expand and crack, and partially solubilizes any powdered active ingredients, causing a glazing of the stick surface. This glaze reduces or eliminates the payout property of the stick, largely rendering it ineffective.

OBJECTS AND SUMMARY OF THE INVENTION

It is accordingly a general object of the present invention to provide a compressed powder formulation which alleviates many of the problems of the prior art.

It is a more specific object of the present invention to provide a compressed powder formulation with an acceptable payout.

It is a further object of the present invention to provide a compressed powder formulation which maintains a substantially constant payout even after being exposed to moisture.

It is a still further object of the present invention to provide a process of preparing a compressed powder formulation which process is efficient and results in an acceptable product.

In one aspect, the present invention provides a compressed powder formulation consisting essentially of:

(a) from about 10 to about 99.95% by weight of an organophilic clay; and (b) from about 0.05 to about 90% by weight of at least one topical agent wherein the compressed powder formulation maintains its physical integrity upon handling, has a payout of from about 10 to about 100 milligrams and retains at least about 90% of its original payout after being contacted with water.

In another aspect, the present invention provides a process for making a compressed powder formulation. The process comprises:

(a) mixing from about 10 to about 99.95% by weight of an organophilic clay and from about 0.05 to about 90% of at least one topical agent to obtain a substantially uniform powderous mixture, and (b) compressing the powderous mixture at a pressure in the range of from about 200 to about 1600 pounds per square inch to obtain a compressed powder formulation which maintains its physical integrity upon handling, has a payout of from about 10 to about 100 milligrams and retains at least about 90% of its original payout after being contacted with water.

DESCRIPTION OF THE PREFERRED EMBODIMENTS

As stated hereinabove, one aspect of the present invention relates to a compressed powder formulation. The compressed powder formulation consists essentially of from about 10 to about 99.95% by weight, preferably from about 40 to 80% by weight of organophilic clay and from about 0.05 to about 90% by weight, preferably from about 20 to about 60% by weight of at least one topical agent.

The organophilic clay used in the present invention may be selected from those organophilic clays well known in the art including those which are commercially available. In particular, the organophilic clay may be the reaction product of a smectitetype clay having a cationic exchange capacity of at about least 75 milliequivalents per 100 grams of clay and at least one organic cation as will be defined below. Illustrative commercially available organophilic clays are illustrated by those available from NL Chemicals, Inc. of Hightstown, N.J. under the trademark "Bentone".

The smectite-type clays are well known in the art and are available from a variety of sources. The clays are preferably converted to the sodium form if they are not already in this form.

This can conveniently be done by preparing an aqueous clay slurry and passing the slurry through a bed of cation exchange resin in the sodium form. Alternatively, the clay can be mixed with water and a soluble sodium compound such as sodium carbonate, sodium hydroxide, etc., and shearing the mixture such as with a pugmill or extruder.

Smectite clays prepared synthetically by either a pneumatolytic or, preferably, a hydrothermal synthesis process can also be used to prepare these novel organic clay complexes. Representative of such clays are the following:

Montmorillonite

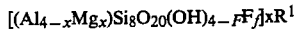
$[(Al_{4-x}Mg_x)Si_8O_{20}(OH)_{4-f}F_f]xR^1$ where $0.55 > x \leq 1.10$, $f \leq 4$ and R is selected from the group consisting of Na, Li, NH$_4$, and mixtures thereof;

Bentonite

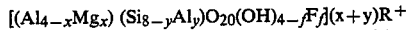
$[(Al_{4-x}Mg_x)(Si_{8-y}Al_y)O_{20}(OH)_{4-f}F_f](x+y)R^+$ where $0 < x < 1.10$, $0 < y < 1.10$, $0.55 \leq (x+y) \leq 1.10$, $f \leq 4$ and R is
selected from the group consisting of Na, Li, NH$_4$ and mixtures thereof;

Beidellite

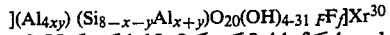
$](Al_{4xy})(Si_{8-x-y}Al_{x+y})O_{20}(OH)_{4-31}fF_f]xR^{30}$ where $0.55 \leq x \leq 1.10$, $0 \leq y \leq 0.44$, $f \leq 4$ and R is selected from
the group consisting of Na, Li, NH$_4$ and mixtures thereof;

Hectorite

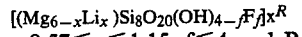
$[(Mg_{6-x}Li_x)Si_8O_{20}(OH)_{4-f}F_f]x^R$ where $0.57 \leq x \leq 1.15$, $f \leq 4$ and R is selected from the group
consisting of Na, Li, NH$_4$, and mixtures thereof;

Saponite

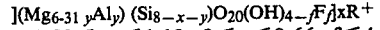
$](Mg_{6-31\ y}Al_y)(Si_{8-x-y})O_{20}(OH)_{4-f}F_f]xR^+$ where $0.58 \leq x \leq 1.18$, $0 \leq y \leq 0.66$, $f \leq 4$ and R is selected from the
group consisting of Na, Li, NH$_4$, and mixtures thereof;

Stevensite

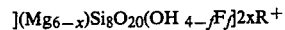
$](Mg_{6-x})Si_8O_{20}(OH_{4-f}F_f)2xR^+$ where $0.28 \leq x \leq 0.57$, $f = 4$ and R is selected from the group
consisting of Na, Li, NH$_4$, and mixtures thereof.

These clays may be synthesized hydrothermally by forming an aqueous reaction mixture in the form of a slurry containing mixed hydrous oxides or hydroxides of the desired metals with or without, as the case may be, sodium (or alternate exchangeable cation or mixture thereof) fluoride in the proportions defined by the above formulas and the preselected values of x, y and f for the particular synthetic smectite desired. The slurry is then placed in an autoclave and heated under autogenous pressure to a temperature within the range of approximately 100° to 325° C., preferably 275° to 300° C., for a sufficient period of time to form the desired product. Formulation times of 3 to 48 hours are typical at 300° C. depending on the particular smectite-type clay being synthesized, and the optimum time can readily be determined by pilot trials. Representative hydrothermal processes for preparing synthetic smectite clays are described in U.S. Pat. Nos. 3,252,757, 3,586,478, 3,666,407, 3,671,190, 3,844,978, 3,844,979, 3,852,405 and 3,855,147, all of which are herein incorporated by reference.

The cation exchange capacity of the smectite clay can be determined by the well-known ammonium acetate method.

The organic cation which is reacted with this smectite-type clay is preferably an ammonium cation which contains at least one lineal or branched, saturated or unsaturated alkyl group having 12 to 22 carbon atoms. The remaining groups of the ammonium cation are chosen from (a) lineal or branched alkyl groups having 1 to 22 carbon atoms; (b) aralkyl groups which are benzyl and substituted benzyl moieties including fused ring moieties having lineal or branched 1 to 22 carbon atoms in the alkyl portion of the structure; (c) aryl groups such as phenyl and substituted phenyl including fused ring aromatic substituents; (d) beta, gamma, unsaturated groups having six or less carbon atoms or hydroxyalkyl groups having two to six carbon atoms; and (e) hydrogen.

The long chain alkyl radicals may be derived from natural occurring oils including various vegetable oils, such as corn oil, coconut oil, soybean oil, cottonseed oil, castor oil and the like, as well as various animal oils or fats such as tallow oil. The alkyl radicals may likewise be petrochemically derived such as from alpha olefins.

Representative examples of useful branched, saturated radicals include 2-methylstearyl; and 12-ethylstearyl. Representative examples of useful branched, unsaturated radicals include 12-methyloleyl and 12-ethyloleyl. Representative examples of unbranched saturated radicals include lauryl; stearyl; tridecyl; myristyl (tetradecyl); pentadecyl; hexadecyl; hydrogenated tallow, docosonyl. Representative examples of unbranched, unsaturated and unsubstituted radicals include oleyl, linoleyl, linolenyl, soya and tallow.

Additional examples of aralkyl, that is benzyl and substituted benzyl moieties would include those materials derived from, e.g. benzyl halides, benzhydryl halides, trityl halides, α-halo-α-phenylalkanes wherein the alkyl chain has from 1 to 22 carbon atoms such as 1-halo-1-phenylethane, 1-halo-1-phenyl propane, and 1-halo-1-phenyloctadecane; substituted benzyl moieties such as would be derived from ortho, meta and para-chlorobenzyl halides, para-methoxybenzyl halides, ortho, meta and para-nitrilobenzyl halides, and ortho, meta and para-alkylbenzyl halides wherein the alkyl chain contains from 1 to 22 carbon atoms; and fused ring benzyl-type moieties such as would be derived from 2-halomethylnaphthalene, 9-halomethylanthracene and 9-halomethylphenanthrene, wherein the halo group would be defined as chloro, bromo, iodo, or any other such group which serves as a leaving group in the nucleophilic attack of the benzyl type moiety such that the nucleophile replaces the leaving group on the benzyl type moiety.

Examples of aryl groups would include phenyl such as in N-alkyl and N,N-dialkyl anilines, wherein the alkyl groups contain between 1 and 22 carbon atoms; ortho, meta and para-nitrophenyl, ortho, metal and para-alkyl phenyl, wherein the alkyl group contains between 1 and 22 carbon atoms, 2-, 3-, and 4-halophenyl wherein the halo group is defined as chloro, bromo, or iodo, and 2-, 3-, and 4-carboxyphenyl and esters thereof, where the alcohol of the ester is derived from an alkyl alcohol, wherein the alkyl group contains between 1 and 22 carbon atoms, aryl such as a phenol, or aralkyl such as benzyl alcohols; fused ring aryl moieties such as naphthalene, anthracene, and phenarthene.

The $\beta, \gamma$-unsaturated alkyl group may be selected from a wide range of materials. These compounds may be cyclic or acyclic, unsubstituted or substituted with aliphatic radicals containing up to 3 carbon atoms such that the total number of aliphatic carbons in the $\beta,\gamma$-unsaturated radical is 6 or less. The $\beta,\gamma$-unsaturated alkyl radical may be substituted with an aromatic ring that likewise is conjugated with the unsaturation of the $\beta,\gamma$ moiety or the $\beta,\gamma$-radical is substituted with both aliphatic radicals and aromatic rings.

Representative examples of cyclic $\beta,\gamma$-unsaturated alkyl groups include 2-cyclohexenyl and 2-cyclopentenyl. Representative examples of acyclic $\beta,\gamma$-unsaturated alkyl groups containing 6 or less carbon atoms include propargyl; allyl(2-propenyl); crotyl(2-butenyl); 2-pentenyl; 2-hexenyl; 3-methyl-2-butenyl; 3-methyl-2-pentenyl; 2,3-dimethyl-2-butenyl; 1,1-dimethyl-2-propenyl; 1,2-dimethyl propenyl; 2,4-pentadienyl; and 2,4-hexadienyl. Representative examples of acyclic-aromatic substituted compounds include cinnamyl(3-phenyl-2-propenyl); 2-phenyl-2-propenyl; and 3-(4 methoxyphenyl)-2-propenyl. Representative examples of aromatic and aliphatic substituted materials include 3-phenyl-2-cyclohexenyl; 3-phenyl-2-cyclopentenyl; 1,1-dimethyl-3-phenyl-2-propenyl; 1,1,2-trimethyl-3-phenyl-2-propenyl; 2,3-dimethyl-3-phenyl-2-propenyl; 3,3-dimethyl-2-phenyl-2-propenyl; and 3-phenyl-2-butenyl.

The hydroxyalkyl group is selected from a hydroxyl substituted aliphatic radical wherein the hydroxyl is not substituted at the carbon adjacent to the positively charged atom, and the group has from 2 to 6 aliphatic carbons. The alkyl group may be substituted with an aromatic ring independently from the 2 to 6 aliphatic carbons. Representative examples include 2-hydroxyethyl (ethanol); 3-hydroxypropyl; 4-hydroxypentyl; 6-hydroxyhexyl; 2-hydroxypropyl (isopropanol); 2-hydroxybutyl; 2-hydroxypentyl; 2-hydroxyhexyl; 2-hydroxycyclohexyl; 3-hydroxycyclohexyl; 4-hydroxycyclohexyl; 2-hydroxycyclopentyl; 3-hydroxycyclopentyl; 2-methyl-2-hydroxypropyl; 1,1,2-trimethyl-2-hydroxypropyl; 2-phenyl-2-hydroxyethyl; 3-methyl-2-hydroxybutyl; and 5-hydroxy-2-pentenyl.

The organic cation can thus be considered as having the following formula:

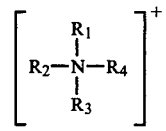

wherein $R_1$ is the long chain alkyl group and $R_2$, $R_3$ and $R_4$ are representative of the other possible groups described above.

The preferred organic cation is where $R_1$ is hydrogenated tallow, $R_2$ is benzyl and $R_3$ and $R_4$ are methyl. Organophilic clay prepared from this organic cation is more fully described in U.S. Pat. No. 4,116,866 which is incorporated by reference and is commercially available from NL Chemicals, Inc. under the trademark Bentone 27.

The amount of organic cation reacted with the smectite-type clay depends upon the specific clay and the desired degree of hydrophobicity. Typically, the amount of cation ranges from about 90 to about 150, preferably from about 95 to about 120 milliequivalents per 100 grams of clay, 100% active basis.

The anion which will normally accompany the organic cation is typically one which will not adversely affect the reaction product or the recovery of the same. Such anions may be exemplified by chloride, bromide, iodide, hydroxyl, nitrite and acetate in amounts sufficient to neutralize the organic cation.

The preparation of the organic cationic salt (i.e., the organic cation paired with the anion) and the organophilic clay can be achieved by techniques well known in the art. For example, when preparing a quaternary ammonium salt, one skilled in the art would prepare a dialkyl secondary amine, for example, by the hydrogenation of nitriles, see U.S. Pat. No. 2,355,356, and then form the methyl dialkyl tertiary amine by reductive alkylation using formaldehyde as a source of the methyl radical. According to procedures set forth in U.S. Pat. No. 3,136,819 and U.S. Pat. No. 2,775,617, quaternary amine halide may then be formed by adding benzyl chloride or benzyl bromide to the tertiary amine. The contents of these three patents are hereby incorporated by reference. As is well known in the art, the reaction with benzyl chloride or benzyl bromide can be completed by adding a minor amount of methylene chloride to the reaction mixture so that a blend of products which are predominantly benzyl substituted is obtained. This blend may then be used without further separation of components to prepare the organophilic clay.

The organophilic clays can be prepared by admixing the clay, the organic cationic salt and water together, preferably at a temperature within the range from about 20° to about 100° C., and preferably from about 35° to about 77° C. for a period of time sufficient for the organic compound to coat the clay particles. Thereafter, the organophilic clay can be subjected to a variety of optional recovery steps such as filtering, washing, drying and grinding.

Illustrative of the numerous patents which describe organic cationic salts, their manner of preparation and their use in the preparation of organophilic clays are commonly assigned U.S. Pat. Nos. 2,966,506, 4,105,578, 4,116,866, 4,208,218, 4,391,637, 4,434,076 and 4,450,095, the contents of which were incorporated by reference.

The organophilic clay used in the present invention may also be the reaction product of the smectite-type clay, the organic cation and an organic anion. The organic anion is selected from a wide range of materials which are capable of reacting with the organic cation in order to form an organic cation/organic anion complex which may be intercalated with the smectite-type clay. The molecular weight (gram molecular weight) of the organic anion is preferably 3,000 or less, and most preferably 1,000 or less and contains at least one acidic moiety per molecule so as to permit the formation of the organic cation/organic anion complex. The organic anion is preferably derived from an organic compound having a $pK_A$ less than about 11.0.

Preferable organic anions are derived from carboxylic acid, such as benzoic acid, sulfonic acids and alkyl sulfates, such as the lauryl half ester of sulfuric acid.

The organic anion, which includes mixtures of organic anions, is reacted with the organic cation and smectite-type clay to form the organophilic clay and may be added to the reaction mixture in acid or salt form. Exemplary of the latter form are alkali metal salts, alkaline earth salts, ammonia and organic amines.

The amount of organic anion reacted with smectite-type clay and the organic cation typically ranges from about 5 to about 100 milliequivalents, preferably from about 10 to about 50 milliequivalents per 100 grams of clay, 100% active basis.

Illustrative patents which describe suitable organic anions which may be co-reacted with the organic cation and the smectite-type clay in order to form the organophilic clay include commonly assigned U.S. Pat. Nos. 4,412,018 and 4,434,075 and allowed application Ser. No. 348,641 filed on Apr. 18, 1982, now U.S. Pat. No. 4,517,112, the contents of all of which are incorporated by reference.

The topical agent used in the compressed powder formulation may be any one or combination of materials commonly applied to a surface, especially the surface of skin. Exemplary topical agents are antiperspirant agents, deodorant agents, pigments, antifungal agents and insect repellants. The formulation may also include conventional fillers and/or processing aids, such as lubricating agents. Of course, the specific ingredient or ingredients used in the compressed powder formulation are selected depending upon the desired end use of the formulation. For example, when the compressed powder formulation is designed to have antiperspirant characteristics, the formulation may contain from about 10 to about 30%, preferably about 15 to about 25% by weight of known antiperspirant agents such as aluminum chlorohydrate, aluminum chlorohydrex, aluminum zirconium chlorohydrate, aluminum zirconium chlorohydrex, aluminum zirconium glycine complexes and mixtures thereof. The preferred antiperspirant agent is aluminum chlorohydrate.

The deodorant agent may be used alone or in combination with the antiperspirant agent and may be present in an amount ranging from about 0.05 to about 10%, preferably from about 0.1 to about 1% by weight. Typical deodorant agents include benzethonium chloride, triclosan, aluminum chlorohydrate, aluminum zirconium chlorohydrate, sodium aluminum chlorhydroxy lactate, cetyl pyridinium chloride, fragrances which will mask odors and mixtures thereof. The preferred deodorant agents are benzethonium chloride and triclosan.

Pigments which may be present in the compressed powder formulation may be any of those known in the art which do not substantially adversely affect the desired characteristics of the formulation. Exemplary pigments are ultramarine blue, chromium oxide green, black iron oxides, titanium dioxides and mixtures thereof. When present, the amount of pigment is from about 0.5 to about 30%, preferably from about 3 to about 15% by weight.

Antifungal agent may be present in the compressed powder formulation in an amount ranging from about 1 to about 10%, preferably from about 3 to about 5% by weight. Exemplary antifungal agents include zinc undecylenate, undecylenic acid and mixtures thereof. The preferred antifungal agent is a mixture of zinc undecylenate and undecylenic acid.

Filler may be present in the compressed powder formulation in order to dilute the concentration of the active ingredients or reduce the cost. Typical fillers include talc, dicalcium phosphate, hydrophobic starch, microcrystalline cellulose and mixtures thereof with the preferred filler being talc. When present, the amount of filler is from about 5 to about 60%, preferably from about 20 to about 40% by weight.

A lubricating agent is used in the compressed powder formulation for the purpose of facilitating the release of the formulation from the compression mold. Typical lubricating agents include magnesium stearate, stearic acid, zinc stearate, calcium stearate and mixtures thereof with the preferred lubricating agent being magnesium stearate. When present, the amount of lubricating agent is from about 0.5 to about 3%, preferably from about 1 to about 2% by weight.

The compressed powder formulation may be prepared by mixing the organophilic clay with the other ingredients in any order. Mixing may be achieved in a conventional mixer, such as a V-Blender, and is conducted for a period of time sufficient to ensure a substantially uniform mixture of the components. Thereafter, the powderous mixture is compressed at a pressure ranging from about 200 to about 1600, preferably from about 250 to about 650 pounds per square inch, such as with a Carver Press, such that a compressed powder formulation which will maintain its physical integrity upon handling is obtained. Both mixing and compressing should be conducted in the substantial absence of free water which can solubilize the ingredients of the formulation which can in turn adversely affect the payout.

The shape of the compressed powder formulation is selected according to the intended use of the formulation. Depending upon the specific ingredients in the formulation, the compressed powder formulation may be made into antiperspirant or antideodorant sticks which are sized and shaped for convenient human use, eye shadows, make-up compacts, make-up sticks, blushes or rouge sticks, aftershave sticks, perfume sticks, talcum powder sticks, antisepticidal sticks or pellets, artistic chalks or foot powder sticks. The preferred formulations are used for antiperspirant and deodorant sticks.

In order for the proper amount of material to be obtained by contact with the compressed powder formulation, it has a payout ranging from about 10 to about 100 milligrams, preferably from about 40 to about 80 milligrams. Payout is determined by attaching a filter paper (whatman #541) securely to the pan of an electronic balance. Using the test material having the dimensions of a cylinder of 28 mm in diameter, the compressed powder formulation is contacted with the surface of the filter paper and pressed down with a force that registers between 50-100 grams on the balance. The stick is drawn across the filter paper 5 times (3 inches in each draw). The force during the draws should register between 50-100 grams. The "payout" corresponds to the total weight of the product deposited on the filter paper after the 5 drawdowns. Naturally, this test should be repeated several times to ensure that the results are consistent.

To a certain extent, payout can be controlled by regulating the molding pressure. Higher molding pressures generally lead to lower payouts and vice-versa. The payout should additionally be substantially uniform as indicated by an absence of large pieces (e.g., greater than one eighth inch in maximum dimension) breaking from the formulation. The absence of such large pieces is a further indication that the compressed powder formulation will maintain its physical integrity upon handling.

An additional benefit of the compressed powder formulation of the present invention is that contact with moisture does not substantially adversely affect its payout property. That is, in contrast to many formulations which tend to exhibit a glazing effect when contacted with moisture, such as may be present in the form of water or perspiration on the skin, the compressed powder formulation of the present invention retains a payout of at least about 90%, preferably at least about 95% of its original payout. This significant advantage may be determined by immersing the pressed powder formulation in room temperature water for 30 seconds, permitting the formulation to completely dry and then conducting the payout test noted above. In those instances wherein the compressed powder formulation does not contain a water soluble ingredient such as aluminum chlorohydrate, the formulation apparently regains its payout value by a simple drying mechanism. However, when a water soluble ingredient is present, the formulation regains its payout value by an exfoliation process wherein the surface cracks and peels off as flakes upon drying thereby revealing fresh surface. From an aesthetic standpoint, it is preferred that the flakes be smaller in size such as in the range of from about 1 to about 3 millimeters in maximum dimension.

As used in the present context, the term "consisting essentially of" excludes amounts of materials which will substantially adversely affect the ability of the formulation to be formed into a compressed body or will substantially adversely affect the compressed powder formulation to substantially regain its payout after being contacted with water.

The following inventive examples and comparative examples are given to illustrate and contrast the present invention. However, the examples should not be construed as limiting the invention. Unless otherwise indicated, all percentages are given in weight percent of the total formulation.

THE ORGANOPHILIC CLAYS

Various organophilic clays are prepared in accordance with the processes briefly described above and more fully disclosed the U.S. patents incorporated by reference. The organophilic clays are all available from NL Chemicals, Inc. of Hightstown, N.J. and have the following designations:

Organophilic Clay A—Bentone 27
Organophilic Clay B—Bentone 34
Organophilic Clay C—Bentone 38
Organophilic Clay D—Bentone SD—1
Organophilic Clay E—Bentone SD—2

SCREENING TESTS

Organophilic Clays A-E along with conventional materials Thixcin R (which is a wax-type product available from NL Chemicals, Inc.), talc, hydrophobic starch and microcrystalline cellulose are compressed into cylindrical sticks from having the dimensions 28 mm in diameter and 20 mm in height using a Carver Press at various pressures. Pressure was varied to try and optimize properties before they were tested to determine if they will maintain their physical integrity upon handling (i.e., absence of crumbling under minimal pressures), have acceptable payout and will retain an acceptable payout after being contacted with water. The results are set forth in Table I.

TABLE I

|  | Pressure (lbs/sq. in) | Physical Integrity | Payout | Effect of Water |
|---|---|---|---|---|
| Organophilic Clay A | 650 | Good | Good | Good |
| Organophilic Clay B | 650 | Good | Good | Good |
| Organophilic Clay C | 650 | Good | Good | Good |
| Organophilic Clay D | 250 | Good | Good | Good |
| Organophilic Clay E | 250 | Good | Good | Good |
| Thixcin R | 200 | Good | No Good | Good |
| Talc | 1600 | No Good | Good | No Good |
| Hydrophobic starch (1) | 1600 | No Good | Good | Good |
| Microcrystalline cellulose (2) | 500 | Good | Good | No Good |

(1) "Dry Flo" available from National Starch Company
(2) "Avicel pH 101" available from FMC Corporation

COMPRESSED FORMULATIONS

Further quantities of Organophilic Clay A are mixed with a variety of types and amounts of conventional additives and the substantially uniform mixture of the ingredients are pressed into a cylindrical stick form having a 28 mm diameter and 20 mm height using a Carver Press at a pressure of 650 pounds per square inch. The resulting sticks are tested to determine if an acceptable payout is maintained after contact with water and the results are set forth in Table II.

TABLE II

| Additive | Additive Function | Payout After Water Contact |
|---|---|---|
| 25% Aluminum Chlorohydrate | Antiperspirant | Acceptable |
| 20% Aluminum Chlorohydrate | Antiperspirant | Acceptable |
| 10% Aluminum Chlorohydrate | Deodorant | Borderline |
| 5% Aluminum Chlorohydrate | Deodorant | Not Acceptable |
| 20% Aluminum Zirconium Tetrachlorohydrex-Gly | Antiperspirant | Acceptable |
| 0.1% Benzethonium Chloride | Deodorant | Acceptable |
| 0.1% Triclosan | Deodorant | Acceptable |
| 2% THIXCIN R | Deodorant | Not Acceptable |
| 1% Magnesium Stearate | Lubricating Agent | Acceptable |
| 10% Talc | Filler | Acceptable |
| 25% Talc | Filler | Acceptable |
| 50% Talc | Filler | Acceptable |
| 100% Talc | Filler | Not Acceptable |

To illustrate the use of combinations of additives, several formulations are prepared using Organophilic Clay A compressed into cylindrical sticks having 28 mm in diameter and 20 mm height by a Carver Press at a pressure of 650 pounds per square inch and are tested for physical integrity, payout and payout after contact with water. The formulations and the results are set forth below.

| Formulation 1 | | |
|---|---|---|
| Organophilic Clay A | 79% | Acceptable |
| Aluminum Chlorohydrate | 20% | |
| Magnesium Stearate | 1% | |
| Formulation 2 | | |
| Organophilic Clay A | 75% | Payout |
| Aluminum Chlorohydrate | 20% | Not Acceptable |
| Stearic Acid | 5% | |
| Formulation 3 | | |
| Organophilic Clay A | 30% | Very Brittle |
| Aluminum Chlorohydrate | 20% | |
| Hydrophobic Starch (1) | 50% | |
| Formulation 4 | | |
| Organophilic Clay A | 40% | Acceptable |
| Aluminum Chlorohydrate | 20% | |
| Talc | 40% | |
| Formulation 5 | | |
| Organophilic Clay A | 99.9% | Acceptable |
| Benzethonium Chloride | 0.1% | |
| Formulation 6 | | |
| Organophilic Clay A | 20% | Acceptable |
| Aluminum Chlorohydrate | 20% | |
| Talc | 60% | |
| Formulation 7 | | |
| Organophilic Clay A | 75% | Acceptable |
| Aluminum Chlorohydrate | 25% | |
| Formulation 8 | | |
| Organophilic Clay A | 80% | Acceptable |
| Aluminum Zirconium Chlorohydrex | 20% | |
| Formulation 9 | | |
| Organophilic Clay A | 50% | Acceptable |
| Aluminum Chlorohydrate | 20% | |
| Microcrystalline Cellulose (2) | 30% | |

(1) "Dry Flo" available from National Starch Company.
(2) "Avicel PH 101" available from FMC Corporation.

The invention being thus described, it will be obvious that the same may be varied in many ways, such variations are not to be regarded as a departure from the spirit and scope of the invention, and all such modifications are intended to be included within the scope of the following claims.

I claim:

1. A dry, compressed powder formulation consisting essentially of:
   (a) from about 10 to about 99.95% by weight of an organophilic clay; and
   (b) from about 0.05% to about 90% by weight of at least one topical agent, wherein the compressed powder formulation is in solid form, maintains its physical integrity upon handling, has a payout which is substantially uniform and which is from about 10 to about 100 milligrams and retains at least about 90% of its original payout after being contacted with water.

2. The compressed powder formulation of claim 1 wherein the topical agent is selected from the group consisting of antiperspirant agents, deodorant agents, pigments, antifungal agents, insect repellants and mixtures thereof.

3. The compressed powder formulation of claim 2 wherein the formulation contains from about 10 to about 30% by weight of antiperspirant agent.

4. The compressed powder formulation of claim 3 wherein the antiperspirant agent is selected from the group consisting of aluminum chlorohydrate, aluminum chlorohydrex, aluminum zirconium chlorohydrate, aluminum zirconium chlorohydrex, aluminum zirconium glycine complexes and mixtures thereof.

5. The compressed powder formulation of claim 4 wherein the antiperspirant agent is aluminum chlorohydrate.

6. The compressed powder formulation of claim 5 wherein the formulation is in the form of a stick adapted for human use.

7. The compressed powder formulation of claim 4 wherein the formulation contains from about 15 to about 25% by weight of the antiperspirant agent.

8. The compressed powder formulation of claim 1 wherein the formulation contains from about 0.05 to about 10% by weight of deodorant agent.

9. The compressed powder formulation of claim 8 wherein the deodorant agent is selected from the group consisting of triclosan, benzethonium chloride, aluminum chlorohydrate, aluminum zirconium chlorohydrate, fragrance, sodium aluminum chlorohydroxy lactate, cetyl pyridinium chloride, and mixtures thereof.

10. The compressed powder formulation of claim 9 wherein the deodorant agent is triclosan or benzethonium chloride in an amount ranging from about 0.1 to about 1% by weight.

11. The compressed powder formulation of claim 1 wherein the organophilic clay is the reaction product of a smectite-type clay having a cation exchange capacity of at least 75 milliequivalents per 100 grams of clay and at least one organic cation having the formula

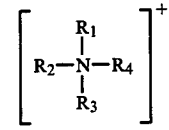

wherein $R_1$ is an alkyl group containing from 12 to 22 carbon atoms, $R_2$ is a benzyl group and $R_3$ and $R_4$ are methyl groups.

12. The compressed powder formulation of claim 11 wherein the smectite-type clay is bentonite or hectorite.

13. The compressed powder formulation of claim 12 wherein the smectite-type clay is hectorite.

14. The compressed powder formulation of claim 11 wherein from about 90 to about 150 milliequivalents of the cation are reacted with each 100 grams of the smectite-type clay.

15. The compressed powder formulation of claim 11 wherein from about 5 to about 100 milliequivalents of an organic anion derived from an organic compound having a $pK_A$ less than about 11.0 is reacted the organic cation and each 100 grams of the smectite-type clay.

16. The compressed powder formulation of claim 15 wherein the organic anion is a mixture of different organic anions.

17. The compressed powder formulation of claim 15 wherein the amount of organic anion ranges from about 10 to about 50 milliequivalents per 100 grams of the smectite-type clay.

18. The compressed powder formulation of claim 1 wherein the payout is in the range of from about 40 to about 80 milligrams.

19. The compressed powder formulation of claim 18 wherein the formulation retains a payout of at least about 95% after being contacted with water.

20. The compressed powder formulation of claim 1 wherein the formulation further comprises at least one of a filler and a lubricating agent.

21. A process for making a dry, compressed powder formulation comprising:
(a) mixing from about 10 to about 99.95% by weight of an organophilic clay and from about 0.05 to about 90% of at least one topical agent to obtain a substantially uniform powderous mixture; and
(b) compressing the powderous mixture at a pressure in the range of from about 200 to about 1600 pounds per square inch to obtain a compressed powder formulation which maintains its physical integrity upon handling, has a payout of from about 10 to about 100 milligrams and retains at least about 90% of its original payout after being contacted with water.

22. The process of claim 21 wherein the formulation is compressed into the form of a stick adapted for human use.

23. The process of claim 21 wherein the formulation is compressed at a pressure in the range of from about 250 to about 650 pounds per square inch.

24. The process of claim 21 wherein the formulation is prepared in the substantial absence of free water.

25. The process of claim 21 wherein the topical agent is selected from the group consisting of antiperspirant agents, deodorant agents, pigments, antifungal agents, insect repellants and mixtures thereof.

26. The process of claim 25 wherein the formulation contains from about 10 to about 30% by weight of an antiperspirant agent.

27. The process of claim 26 wherein the antiperspirant agent is aluminim chlorohydrate.

28. The process of claim 27 wherein the formulation has a payout of from about 40 to about 80 milligrams.

* * * * *